US010226240B2

(12) United States Patent
Fels et al.

(10) Patent No.: US 10,226,240 B2
(45) Date of Patent: Mar. 12, 2019

(54) INVASIVE INSTRUMENT FOR TREATING VESSELS

(75) Inventors: Esther Fels, Berlin (DE); Marsha Wilke, Berlin (DE); Nils Gelbert, Berlin (DE); Johannes Tschepe, Berlin (DE); Karl-Heinz Schönborn, Berlin (DE)

(73) Assignee: W.O.M. WORLD OF MEDICINE GMBH, Berlin (DE)

( * ) Notice: Subject to any disclaimer, the term of this patent is extended or adjusted under 35 U.S.C. 154(b) by 1359 days.

(21) Appl. No.: 13/820,542

(22) PCT Filed: Apr. 19, 2011

(86) PCT No.: PCT/EP2011/056222
§ 371 (c)(1),
(2), (4) Date: May 31, 2013

(87) PCT Pub. No.: WO2011/131660
PCT Pub. Date: Oct. 27, 2011

(65) Prior Publication Data
US 2013/0274548 A1    Oct. 17, 2013

(30) Foreign Application Priority Data
Apr. 23, 2010   (DE) .......................... 10 2010 028 167

(51) Int. Cl.
*A61B 1/00*     (2006.01)
*A61B 17/00*    (2006.01)
(Continued)

(52) U.S. Cl.
CPC .... *A61B 17/00008* (2013.01); *A61B 1/00165* (2013.01); *A61B 1/018* (2013.01);
(Continued)

(58) Field of Classification Search
CPC ............. A61B 1/018; A61B 17/00234; A61B 1/00082; A61B 17/00008; A61B 1/00087;
(Continued)

(56) References Cited

U.S. PATENT DOCUMENTS

| | | | |
|---|---|---|---|
| 5,722,934 A | 3/1998 | Knight et al. | |
| 5,928,138 A | 7/1999 | Knight et al. | |
| 5,984,937 A | 11/1999 | Morse et al. | |
| 6,022,313 A | 2/2000 | Ginn | |

(Continued)

FOREIGN PATENT DOCUMENTS

| | | |
|---|---|---|
| EP | 1 323 373 A2 | 7/2003 |
| EP | 2 116 1189 A1 | 7/2003 |

(Continued)

*Primary Examiner* — Timothy J Neal
(74) *Attorney, Agent, or Firm* — Maschoff Brennan

(57) ABSTRACT

An invasive instrument for treating a vessel, which possibly includes secondary vessels, has a tip formed for the dissection of tissue at the distal end of a shaft to be introduced into the body, with at least one functional unit. The tip includes vessel receptacle means, arranged and formed such that, in the operating condition of the instrument, the functional unit of the shaft is kept clear, so that working on the vessel, a secondary vessel and/or on the surrounding tissue is possible using or by means of the functional unit and with the vessel receiving means the vessel can be fixed in a spatial position. The tip is movable relative to the shaft by means of a guide element and the tip is shiftable in axial direction, so that during the procedure a vessel arranged in the vessel receiving means can be spaced selectively from the functional unit.

16 Claims, 16 Drawing Sheets

(51) Int. Cl.
*A61B 17/02* (2006.01)
*A61B 1/018* (2006.01)
*A61B 1/05* (2006.01)
*A61B 1/06* (2006.01)
*A61B 1/07* (2006.01)
*A61B 1/12* (2006.01)
*A61B 90/00* (2016.01)

(52) U.S. Cl.
CPC ............ *A61B 1/051* (2013.01); *A61B 1/0676* (2013.01); *A61B 1/0684* (2013.01); *A61B 1/07* (2013.01); *A61B 1/126* (2013.01); *A61B 17/0218* (2013.01); *A61B 2017/00805* (2013.01); *A61B 2017/00902* (2013.01); *A61B 2090/064* (2016.02)

(58) Field of Classification Search
CPC ... A61B 1/00193; A61B 1/0055; A61B 1/051; A61B 1/00165; A61B 1/07; A61B 1/0684; A61B 1/0676; A61B 1/126
USPC .................... 600/104, 129, 158, 209; 606/29
See application file for complete search history.

(56) References Cited

U.S. PATENT DOCUMENTS

| | | | |
|---|---|---|---|
| 6,042,538 | A | 3/2000 | Puskas |
| 6,264,670 | B1 | 7/2001 | Chin |
| 7,645,289 | B2 * | 1/2010 | Bayer ........................ 606/159 |
| 8,241,210 | B2 * | 8/2012 | Lunsford ............. A61B 1/3137 600/209 |
| 2002/0099259 | A1 | 7/2002 | Anderson et al. |
| 2003/0130675 | A1 | 7/2003 | Kasahara et al. |
| 2005/0010242 | A1 * | 1/2005 | Lindsay ........................ 606/154 |
| 2009/0143640 | A1 * | 6/2009 | Saadat ............... A61B 1/00089 600/104 |
| 2011/0046624 | A1 | 2/2011 | Lin |

FOREIGN PATENT DOCUMENTS

| | | |
|---|---|---|
| EP | 1323373 B1 | 9/2005 |
| WO | 00/40139 A1 | 7/2000 |
| WO | 01/62183 A1 | 8/2001 |
| WO | 02/19945 A2 | 3/2002 |
| WO | 03/013367 A2 | 2/2003 |
| WO | 2005/094741 A1 | 10/2005 |
| WO | 2006/046950 A1 | 5/2006 |
| WO | 2011/082287 A | 7/2011 |

* cited by examiner

INVASIVE INSTRUMENT FOR TREATING VESSELS

CROSS-REFERENCE TO A RELATED APPLICATION

This application is a National Phase Patent Application of International Patent Application Number PCT/EP2011/056222, filed on Apr. 19, 2011, which claims priority of German Patent Application Number 10 2010 028 167.0, filed on Apr. 23, 2010.

BACKGROUND

This invention relates to an invasive instrument for treating vessels and to a method.

It is known to harvest the endogenous vessels used for a bypass, i.e. veins and arteries, by an invasive, frequently also minimally invasive method under endoscopic control. This method is called Endoscopic Vessel Harvesting (EVH). In this method, especially developed instruments are employed.

Before the actual vessel harvesting takes place, the vessel must be separated from the tissue enclosing the vessel. First, an access is created by means of a small cut in direct vicinity of the vessel to be harvested, for example for harvesting the Vena saphena magna in the region of the knee-joint gap. Subsequently, the introduction of a suitably shaped instrument and the stepwise separation (dissection) by advancing along the vessel axis are effected under visual control and/or endoscopic view.

The known instruments can be used e.g. with an endoscope and/or a camera. From the patent specification U.S. Pat. No. 6,042,538 it is known that an endoscope optics can be integrated into the instrument. The instrument can be formed both as disposable and as reusable product. In a reusable product, the endoscope optics also can inseparably be integrated into the instrument.

Corresponding to the prior art, the endoscope which frequently is integrated into the instrument is connected with a video camera, so that the treating physician can observe his actions on a screen.

From the patent specification U.S. Pat. No. 5,928,138 it is known that a tip can be fabricated of a visually transparent material, so that during the dissection a good forward visibility is ensured for the operating surgeon via the endoscope. Such a transparent tip also is referred to as optical dissector.

The vessel to be harvested is connected with further, smaller peripheral vessels and after dissection from the surrounding tissue must also be separated from said vessels.

According to the prior art, this is effected by cutting devices integrated into the instrument. From the patent specification U.S. Pat. No. 6,022,313 it is known that such cutting device can be designed e.g. with scissors, which are advanced in a working channel of the instrument.

From the patent specification U.S. Pat. Nos. 5,928,138 and 6,022,313 it is known that devices for guiding the vessel to be harvested can be integrated into the instrument.

From the patent specification U.S. Pat. No. 7,645,289 it is known that a transparent tip can be shifted along the longitudinal axis of the instrument by means of a manipulator integrated at the handle. In addition, it is known from the patent specification U.S. Pat. No. 7,645,289 that the side of the tip facing the instrument is provided with a cutout. The design of the cutout allows the accommodation and/or fixation of the peripheral vessels to be separated.

It is furthermore known to support the endoscopically assisted vessel harvesting by means of $CO_2$ gas insufflation. It is known that $CO_2$ gas can selectively be introduced into the body through cavities and/or channels of an instrument for endoscopic procedures.

SUMMARY

It is the object to create an instrument for the invasive, preferably endoscopic treatment, in particular for harvesting vessels, with which in particular surrounding tissue can efficiently be treated in situ.

This object is solved by an invasive instrument for treating a vessel, which possibly includes secondary vessels, with a tip formed for the dissection of tissue at the distal end of a shaft to be introduced into the body. The tip includes at least one recess, in particular a vessel receptacle, which is arranged and formed such that in the operating condition of the instrument always at least one functional unit of the shaft is kept clear, so that working on the vessel, a secondary vessel and/or on the surrounding tissue is possible using or by means of the functional unit. By keeping clear a functional unit (e.g. a working channel for a cutting device), it is easier for the treating physician to work in situ, e.g. without having to replace the tip. With an instrument designed in this way, several functions can be carried out at the same time, such as e.g. holding the vessel (i.e. the vessel receptacle for the main vessel) and simultaneously working on the secondary vessel and/or on the surrounding tissue.

Advantageously, the tip at least partly includes a conical region, a prismatic region, a region in the form of a dolphin nose, a region with a frustoconical shape and/or a region with the shape of a triangle. With these shapes, an efficient dissection of the surrounding tissue can be achieved.

In a further advantageous embodiment, the vessel to be treated can be fixed in a spatial position with the at least one vessel receiving means, wherein the tip is movable relative to the shaft by means of a guide element. After introducing the invasive instrument into the body, the treating physician hence can perform e.g. a preparation of the vessel in situ.

It is also advantageous when the tip is shiftable in axial direction and/or pivotable about the longitudinal axis by up to 180°, so that during the procedure a vessel arranged in the at least one vessel receiving means can be spaced selectively in particular from a cutting device. By creating a rather large distance between vessel and e.g. a cutting device, the risk of a damage of the vessel is minimized. Spacing can also be expedient for other functional units, e.g. an endoscope, since a large visual range hence can be adjusted in situ.

For the handling of the tip it is advantageous when a manipulator is arranged in particular at a handle. With the same, shifting in axial direction and/or rotating the tip can be effected selectively.

Furthermore, it is advantageous when the guide element is formed substantially rod-shaped and is attached at a point of the tip which is located opposite the vessel receiving means. By a rather large spacing between the pivot point of the tip and the vessel receiving means it is possible to turn the vessel receiving means far away from functional units in the shaft. It is also advantageous that the guide channel and the working channel are arranged on opposite sides of the shaft.

Functional units which can be arranged in the shaft and/or in the handle of the instrument are formed at least as an endoscope channel, at least as a working channel for receiving a cutting device, at least as a guide channel for receiving a guide element, at least as an irrigation channel and/or at least as an insufflation channel.

It is also advantageous when the tip with the recess is designed such that the cutting device and/or an endoscope can be moved past the tip in an axially retracted position and/or also in an axially extended position.

Advantageously, the distance between extended tip and instrument tip is adjustable steplessly or in discrete steps. In this way, a particularly efficient preparation of the vessel can be achieved.

It is advantageous when the handle and/or the shaft are designed as reusable instrument. It is also advantageous when the tip, the guide rod and/or the manipulator (13) are designed as disposable components.

For working in situ it is advantageous when at least one channel for conducting rinsing liquid and/or for sucking off undesired liquids is integrated in the shaft.

Advantageously, the endoscope tip protrudes out of the instrument tip and into the retracted transparent tip.

In particular for cleaning purposes it is advantageous when gas, in particular $CO_2$ gas for the insufflation, can be passed to the instrument tip in an insufflation channel. It is particularly advantageous when the insufflation channel and/or the irrigation channel are arranged relative to the endoscope tip such that the endoscope tip can be cleaned with the gas and/or the rinsing liquid, in particular by diverting the gas stream and/or the liquid stream on the back of the tip and directing the same to the endoscope tip.

In a further development, a video camera is arranged at the instrument tip, wherein the video camera includes a video sensor, e.g. a CCD or CMOS sensor, along with associated electronics and suitable optics, and glass fibers, a flexible optical waveguide and/or a solid polymer rod are guided in a separate illumination channel from the handle via the shaft to the instrument tip.

For a good illumination in situ it is particularly advantageous when LEDs are arranged at the instrument tip for illumination.

It is furthermore advantageous when the shaft at least partly has a circular or elliptical cross-section. An elliptical cross-section can be advantageous for the arrangement of the instruments in the interior of the shaft. The shaft possibly can also be formed slightly flatter than would have been the case with a circular cross-section.

BRIEF DESCRIPTION OF THE DRAWINGS

Further embodiments are subject-matter of the sub-claims and/or will be described in more detail below with reference to the Figures, in which

DETAILED DESCRIPTION

Figure 1:
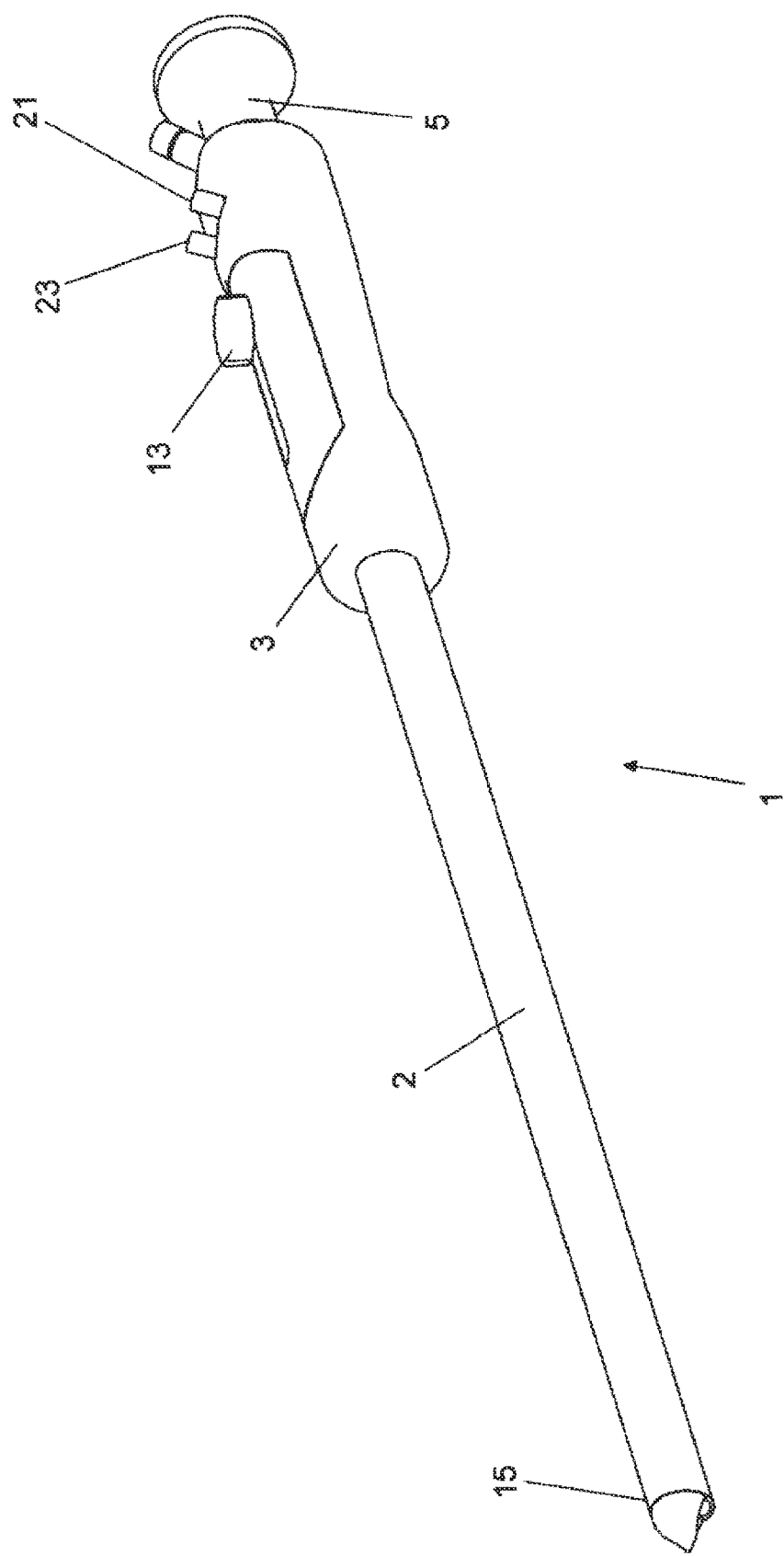
FIG. 1 shows a schematic perspective representation of an embodiment of the instrument for treating, in particular harvesting a vessel.

FIG. 1 shows the basic structure of an embodiment of an invasive instrument 1, in particular for harvesting vessels 14.

In the following an instrument is described, which is particularly formed for harvesting vessels such as the Vena saphena magna (see FIG. 4). In principle, the dimensions of the instrument 1 can be adapted to the conditions of the body.

Other human vessels 14, which can be treated for example with the instrument 1, include the Vena saphena parva (subcutaneous calf vein), the Vena cephalica brachii & antebrachii (subcutaneous vein of the upper and lower arm) or the Vena basilica (deep vein in the upper arm). The invention is, however, not limited to the treatment of these vessels 14.

The instrument 1 serves to invasively treat a vessel 14 (also referred to as main vessel) in the body of a human being (possibly also of an animal) (dissection), so that it can be harvested from the body.

The instrument 1 includes a shaft 2 to be introduced into the body and a handle 3 at the proximal end. At the distal end of the shaft 2 (instrument tip 15) a tip 10 of transparent material is arranged, whose shape and function will yet be explained below.

Figure 2:
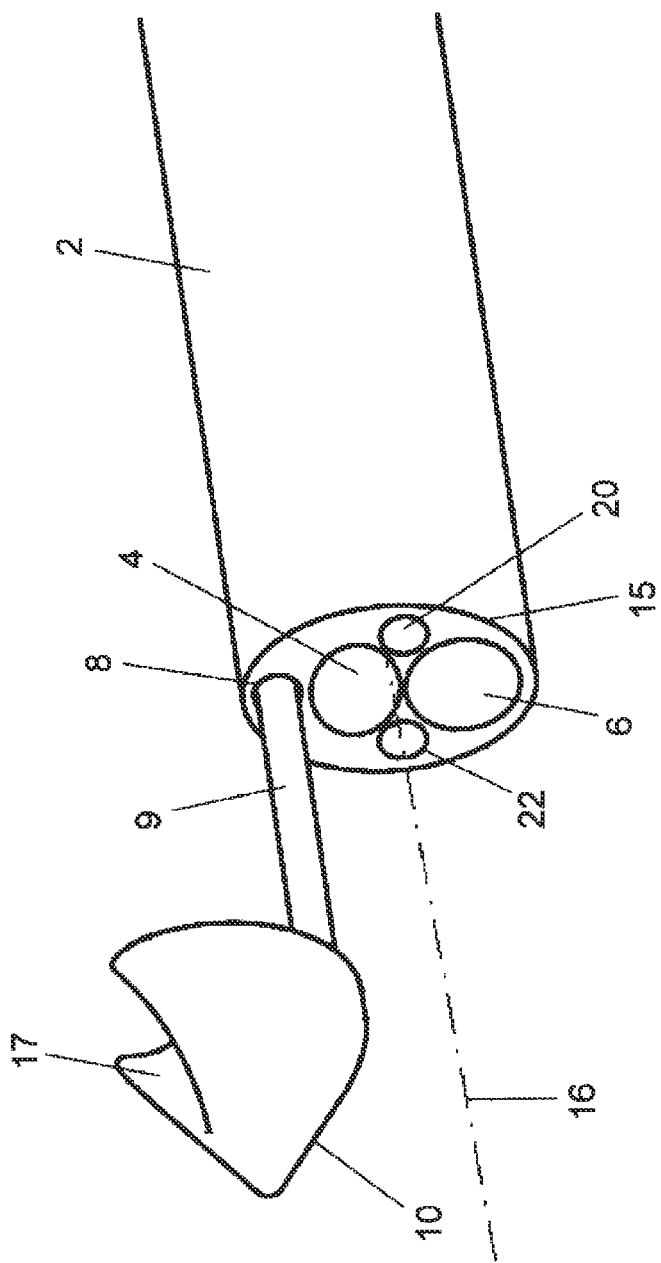
FIG. 2 shows a tip of an embodiment of the instrument.

As shown in connection with FIG. 2, various functional units are arranged in the shaft 2. In the present example, these functional units include an endoscope channel 4 for receiving an endoscope 5 (here not shown for reasons of clarity), a working channel 6 for receiving a cutting device 7 (here not shown for reasons of clarity), as well as a guide channel 8 for receiving a guide element 9 (e.g. in the form of a guide rod 9, here not shown for reasons of clarity), which serves the manipulation of the transparent tip 10. The term functional units comprises devices in, at and/or on the shaft 2 of the instrument 1, with which work and/or observations can be made in particular in the body and/or parts of the instrument 1 can be moved, cleaned (see e.g. FIG. 12) and/or adjusted. The functional unit comprises both regions for receiving devices (e.g. channels) and regions in which devices are arranged (e.g. cutting device 7 in cutting channel 6).

In alternative embodiments, the functional units in the shaft 2 can be arranged otherwise or also be realized in another number. For example, two or more working channels 6 can be present.

In the embodiment shown in FIG. 2, the working channel 6 and the guide channel 8 are located away from each other as far as possible, i.e. on opposite sides of the shaft cross-section.

The transparent tip 10 substantially has a basic structure with a conical part, wherein a vessel receiving means 17 in the form of a recess (or also depression) is arranged at the circumference. The recess 17, or in this case the vessel receiving means 17 with an anatomically shaped receptacle for the vessels 14, has a dual function which will yet be explained in connection with FIGS. 4 and 5.

The tip 10 is formed such that a separation of tissue is possible with the same when it is introduced into the body. In the embodiment shown here, the tip 10 is slightly rounded, in order to avoid damages at the tissue to be separated. As will be shown later on with reference to examples, the tip 10 also can assume other shapes.

The cross-section of the shaft 2 and the base surface of the tip 10 are formed circular in this embodiment. In principle, it is also possible that the shaft 2 and the tip 10 have polygonal or elliptical cross-sections. In this case, transparent means that the tip 10 is transparent for those wavelengths at which an observation takes place. For an endoscopic observation with a usual video camera, e.g. optically transparent polymers (e.g. PMMA) can be used. The tip 10 is hollow from inside, so that the wall thickness of the tip 10 everywhere substantially is the same. This is expedient, in order to ensure a best possible observability with an endoscope 5 through the transparent tip 10.

The connecting point between guide element 9 and transparent tip 10 is not located in the middle axis of the substantially conical body of the transparent tip 10, but offset laterally. As can be seen in FIG. 2, the connecting point is arranged spatially opposite the vessel receiving means 17 in the vicinity of the circumference of the transparent tip 10. In the position of the transparent tip 10 as shown in FIG. 2, the vessel receiving means 17 points upwards. The tip is formed such that in this position it also keeps clear at least one functional unit, in this case several functional units.

Figure 5:
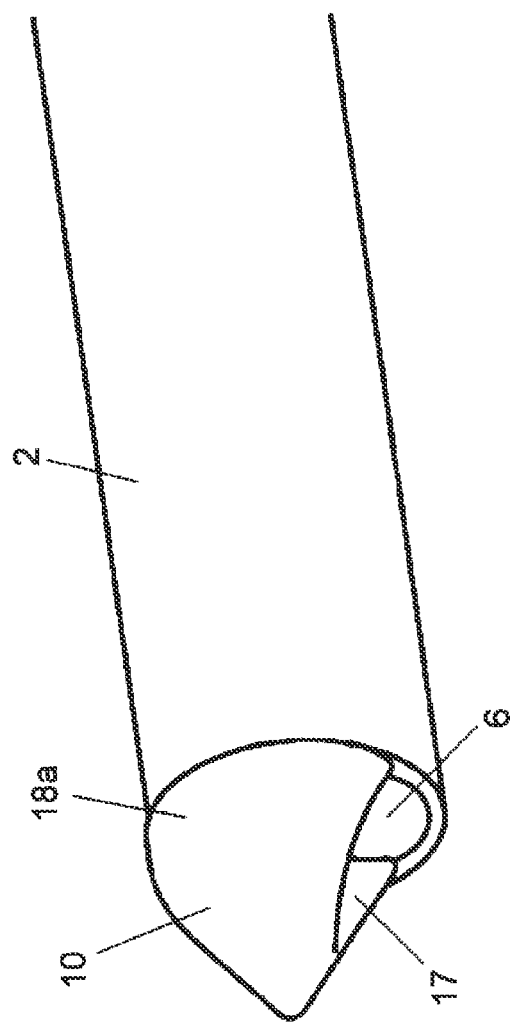
FIG. 5 shows the tip of an embodiment with non-extended tip.

When the transparent tip 10 is rotated by 180° by means of the guide element 9, the concave vessel receiving means 17 points downwards. As can be seen in FIG. 5, the working channel 6 also is free in this position, i.e. the recess 17 (i.e. the vessel receiving means) keeps clear at least one functional unit, here the working channel 6, also in this position.

Hence it becomes clear that the vessel receiving means 17 as recess has a dual function. On the one hand, it ensures that also in the operating position shown in FIG. 5 at least one functional unit is kept clear (e.g. the working channel 6). On the other hand, the recess of the vessel receiving means 17 serves as positioning means for the vessel 14 (i.e. the main vessel), i.e. by rotating the tip 10 with the vessel receiving means 17 the vessel 14 can be brought into a position in which it can easily be treated.

In alternative embodiments, there can also be provided more than one endoscope channel 4, more than one working channel 6 and/or more than one guide channel 8.

Figure 3:
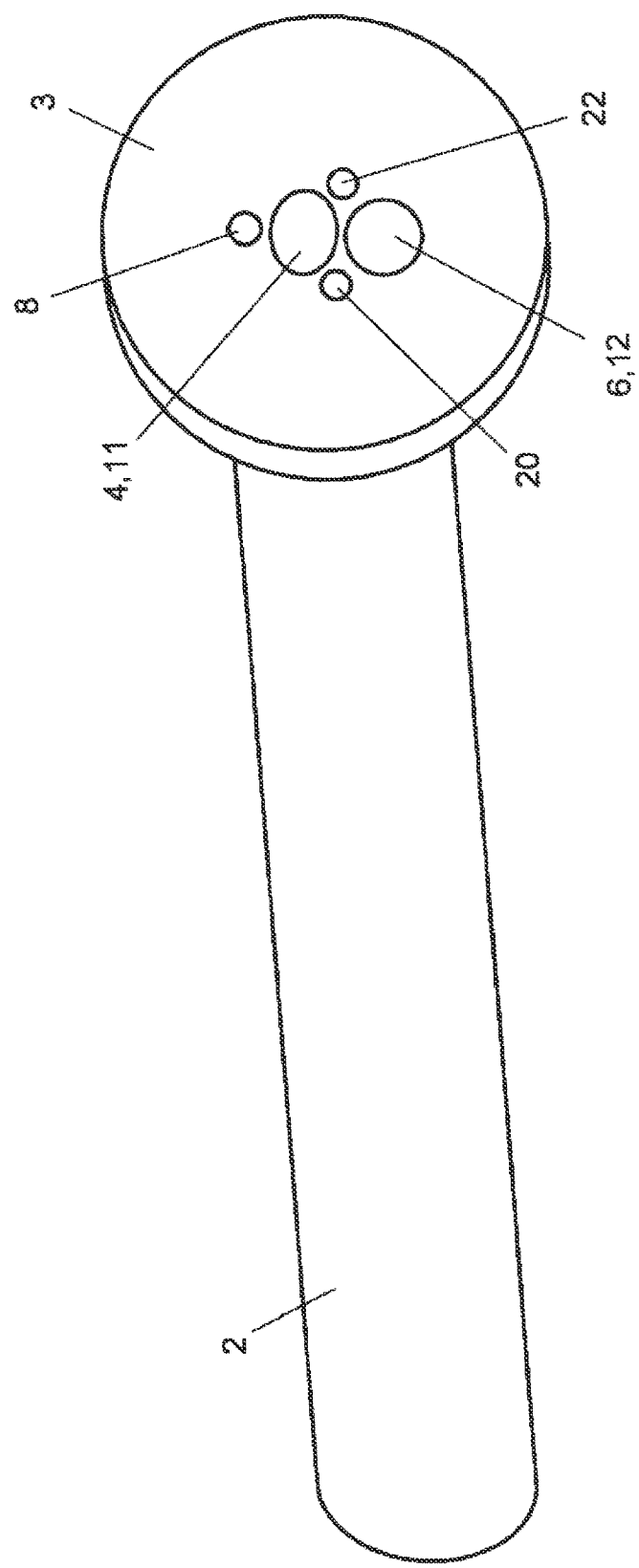
FIG. 3 shows a sectional view through the handle of an embodiment of the instrument.

In the sectional view of FIG. 3 it can be seen that at the handle 3 an opening 11 of the endoscope channel 4 for receiving the endoscope 5, an opening 12 of the working channel 6 and a manipulator 13 connected with the guide element 9 are arranged.

In the following, the function of the design will be explained above all with respect to FIG. 4.

When a vessel 14 is to be separated from the surrounding tissue (not shown in FIG. 4), the transparent tip 10 is arranged at the shaft 2 such that the base line of the tip 10 approximately corresponds to the circumference of the shaft (see e.g. FIG. 5); the tip 10 is flush with the shaft 2.

The transparent tip 10 here is designed such that a vessel 14 to be harvested can be picked up or held by the tip 10 such that it is kept away from the cutting device 7, which is arranged in the working channel 6, and/or is protected against inadvertent damage.

Figure 4:
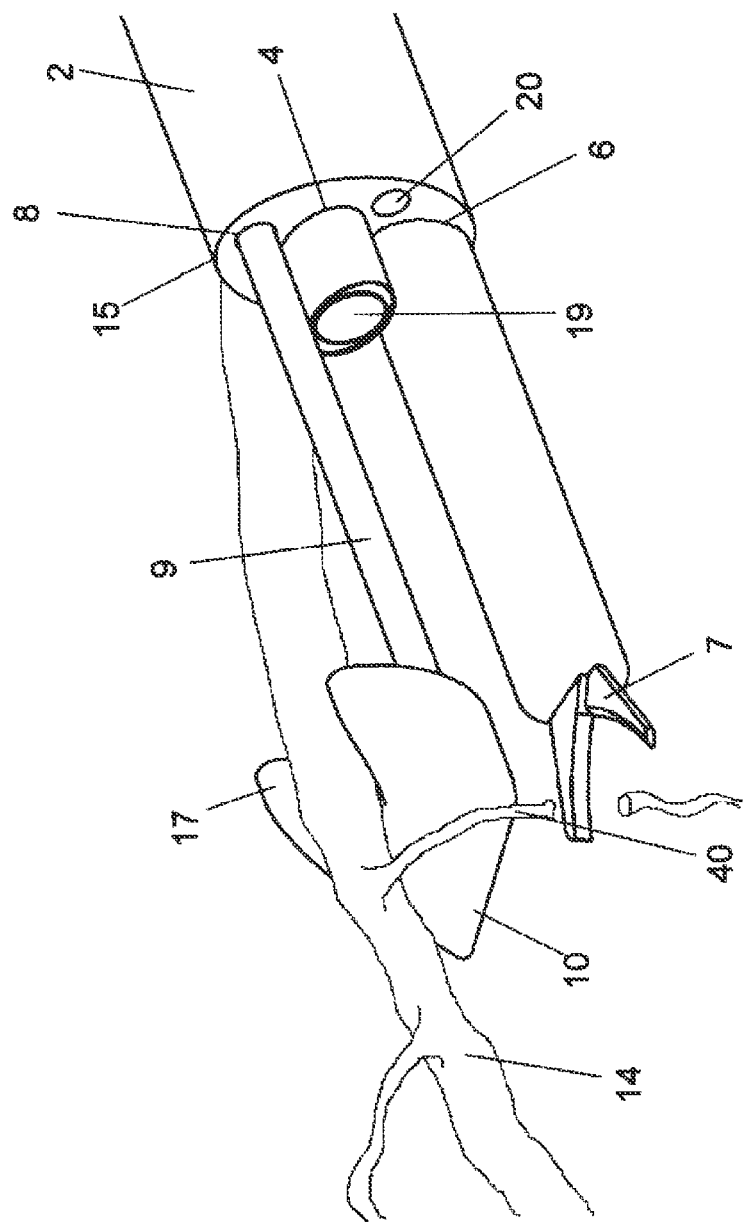
FIG. 4 shows the use of an embodiment of the instrument.

For this purpose, the transparent tip 10 (with the vessel receiving means 17 pointing downwards) is moved by means of the manipulator 13 (see FIG. 1) via the guide element 9 away from the side of the instrument tip 15 facing the vessel 14, along the instrument axis, i.e. the longitudinal axis of the shaft 2 (see FIGS. 2 and 4). This means that the transparent tip 10 is extended from proximal to distal in axial direction.

The manipulator 13 (see FIG. 1) here acts as a kind of sliding mechanism, with which the guide element 9 and hence the transparent tip 10 can be moved in the body in axial direction, and as rotary mechanism (e.g. with a wheel) with which a rotatory movement can be performed. In principle, the manipulator 13 also can be distributed to several operating elements.

After positioning the transparent tip 10 in axial direction, the transparent tip 10 is pivoted by means of the manipulator 13 about the axis of the guide element 9 by up to 180°, so that the vessel 14 is arranged in the depression-like vessel receiving means 17 (see also FIG. 2) and is kept away from the cutting device 7.

The cutting device 7 then can, as shown in FIG. 4, cut through e.g. secondary vessels 40, wherein the cutting device 7 can move freely in axial direction. In FIG. 4, a scissor device is used as cutting device 7. In principle, however, other cutting means are also conceivable.

In alternative embodiments, the vessel receptacle 17 can be formed as notch or as U-shaped indentation. In any case, it is possible to dispose the vessel 14 in a vessel receptacle 17 such that it cannot easily slip out laterally.

It is possible to adjust the axial distance between the extended transparent tip 10 and the instrument tip 15 by means of the manipulator 13 and the guide rod 9 steplessly or in discrete steps.

Figure 6:
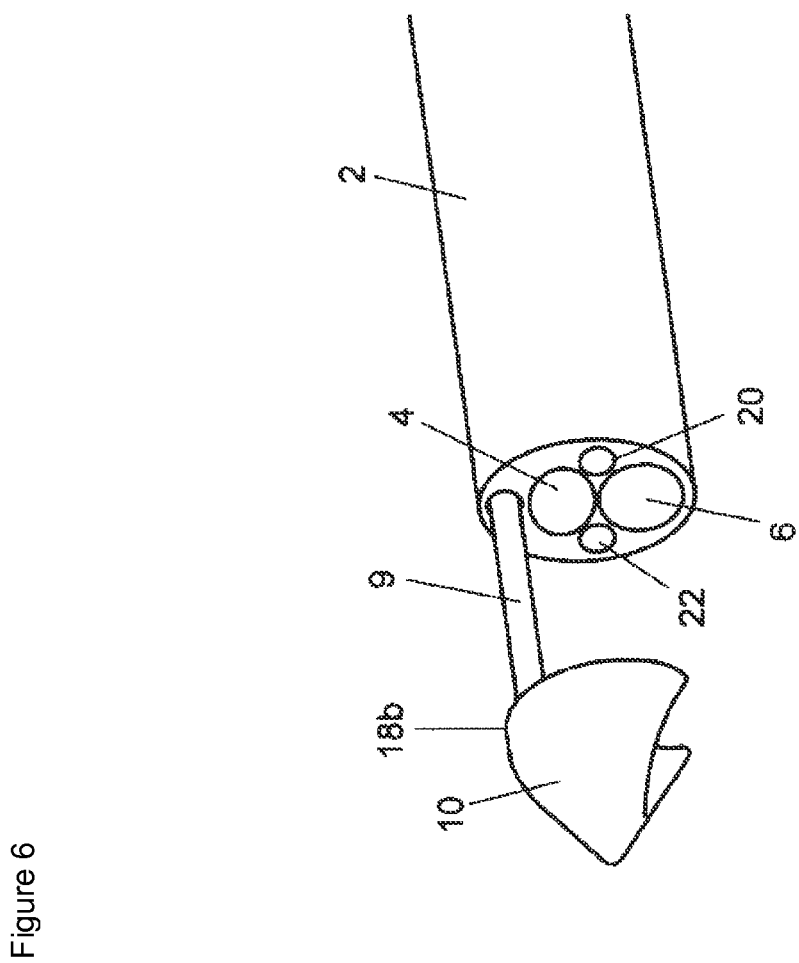
FIG. 6 shows the tip of an embodiment of the instrument with a tip extended axially in a distal direction.

With the illustrated embodiment it is possible that the transparent tip 10 is designed such that both in the retracted position 18a (see FIG. 5) and in the extended position 18b (see FIG. 6) the cutting device 7 can be guided past the tip 10. In FIGS. 5 and 6 it is shown that the receiving means 17 is formed in the tip 10 such that the depression-like formation does not cover the working channel 6.

This allows the operating surgeon to prepare vessels 14, secondary vessels 40, and also separate the same from the surrounding tissue, during each phase of the procedure. The tip 10 is formed such that in each phase a functional unit, here the working channel 6 with the cutting device 7 arranged therein, is operable.

The operating surgeon even can axially move the cutting device 7 further in distal direction beyond the tip 10, in order to cut before the actual instrument 1 and/or the tip 10. The vessel receiving means 17 then can be used to spatially fix the vessel 14 in a position in which an operating surgeon can work particularly well. The rotatability of the guide element 9 allows an arbitrary positioning, wherein in each case the necessary distance to the cutting device 7 is maintained. Due to the axial shiftability and/or rotatability (i.e. movements relative to the shaft 2), it is also possible to align the vessel 14 with the attached secondary vessels 40 such that a preparation or separation of the secondary vessel 40 is possible.

This allows in particular the vessel harvesting without change of the instrument and/or removal of the transparent tip 10.

Figure 5A:
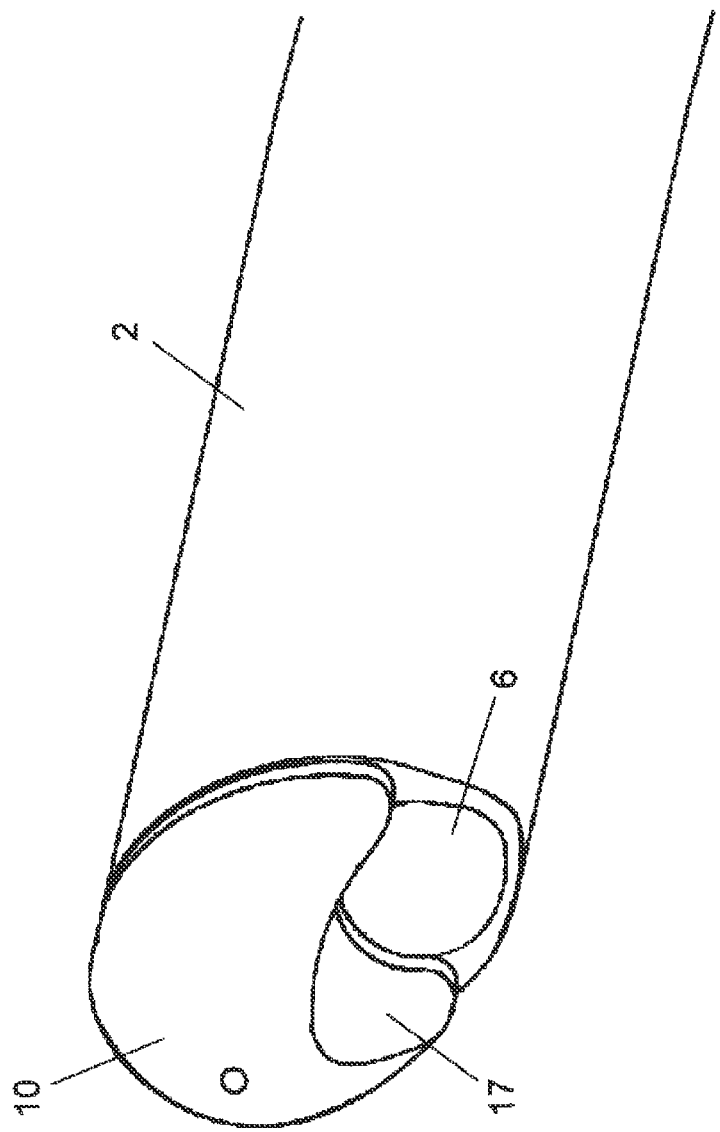
FIG. 5a shows a modified embodiment according to FIG. 5.

FIG. 5a shows a modification of an embodiment which is shown in FIG. 5, in a slightly different perspective. The vessel receptacle 17 here is turned downwards, so that the functional unit, in this case the working channel 6, is exposed in axial direction through the recess of the vessel receptacle 17. Thus, the tip 10 with the recess 17 cannot only be used for holding or placing vessels 14, but due to the recess 17 the tip 10 also is designed such that the functional units are exposed.

In a further exemplary embodiment of the instrument 1, the components handle 3 and/or shaft 2 are designed as reusable instrument. The same are shaped such that they can be prepared mechanically and subsequently be sterilized with commonly used sterilization methods, in particular the steam sterilization. The tip 10, the guide element 9 and/or the manipulator 13 can be designed as disposable components and due to their modular construction can easily be mounted in the reusable instrument and again be removed from the same.

Figure 7:
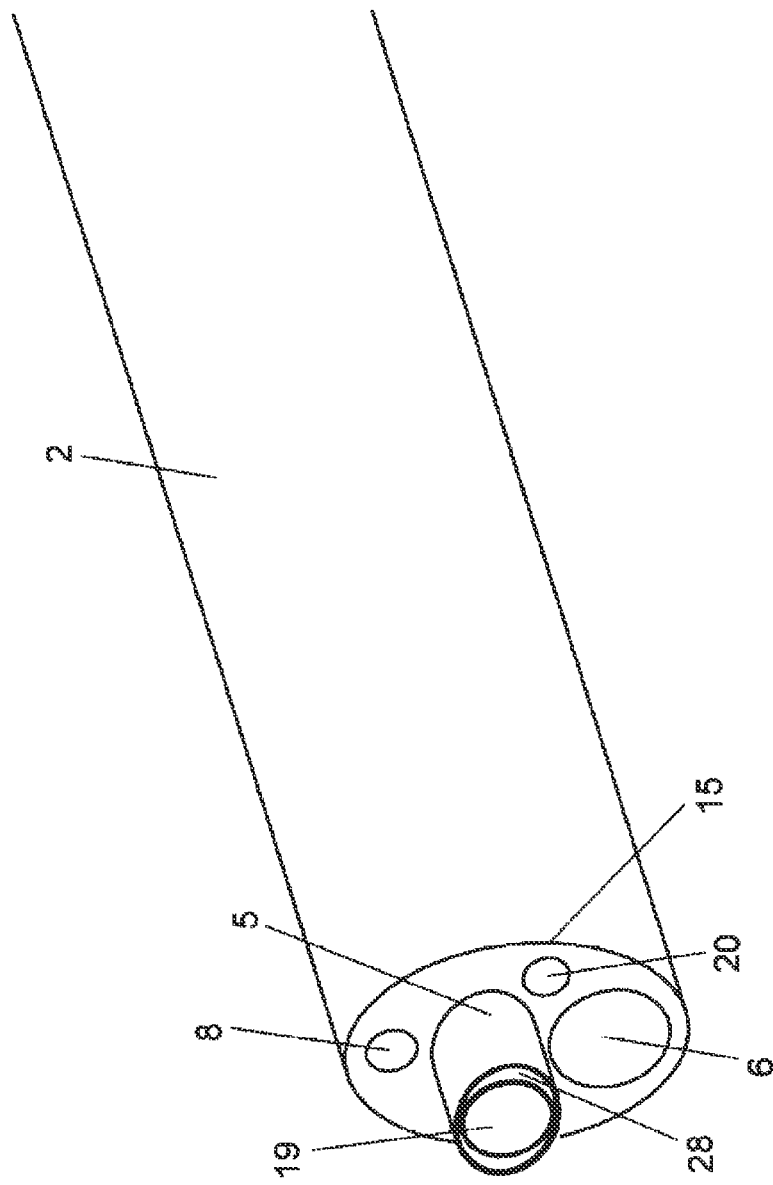
FIG. 7 shows an embodiment with an irrigation channel.
Figure 12:
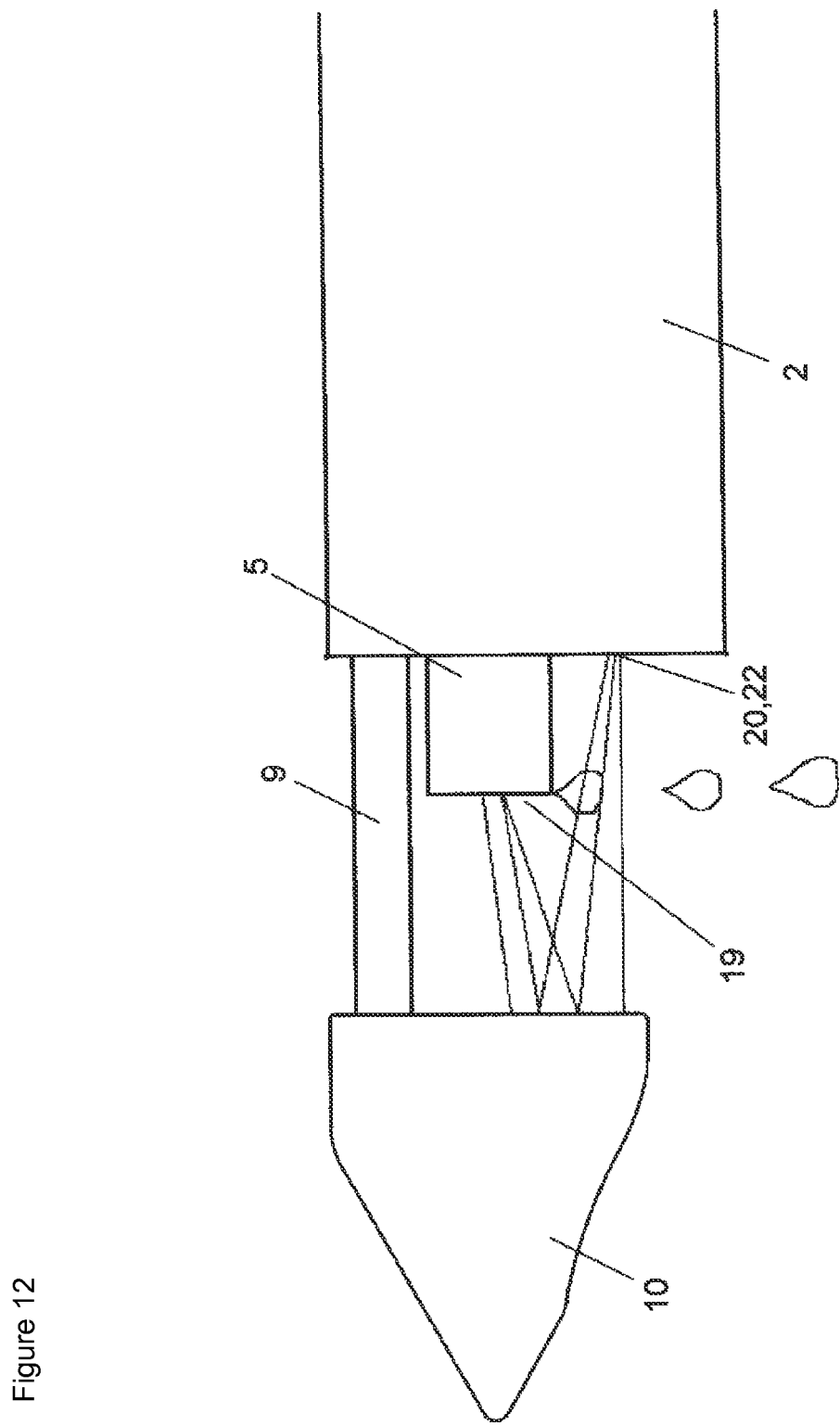
FIG. 12 shows a detail of a further embodiment concerning the flow pattern of purge gas.

In a further embodiment (see FIG. 7), an irrigation channel 20 for supplying and sucking off rinsing and body fluids is arranged in the shaft 2, so that a tip 19 of the endoscope 5 and the transparent tip 10 can be cleaned in situ by means of an irrigation. The effect of cleaning is intensified when—as shown in FIG. 12—the endoscope tip 19 protrudes out of the instrument tip 15 and into the retracted transparent tip 10. The irrigation channel 20 ends in the handle in a port 21 for supplying and sucking off rinsing and body fluids (see FIG. 1).

A further exemplary embodiment (see FIG. 12) allows that $CO_2$ gas (or also another gas) for the insufflation is passed to the instrument tip 15 in an integrated insufflation channel 22 as functional unit. The position of the insufflation channel 22 relative to the endoscope tip 19 is to be arranged such that with the $CO_2$ gas the endoscope tip can be liberated from undesired liquid. By way of example, this can be realized in that the $CO_2$ gas stream is diverted on the back of the transparent tip 10 and directed to the endoscope tip 19. The channel 22 ends in the handle in a port 23 (see FIG. 1). FIG. 12 also shows a rinsing function with which a rinsing liquid is sprayed from an irrigation channel 20. In the side view of FIG. 12, irrigation channel 20 and insufflation channel 22 can only be seen laterally at the exit of the jets. In a further exemplary embodiment, the instrument 1 is designed as disposable instrument, wherein the instrument 1 in principle can have the same shape and function as described above. For this purpose, the components handle 3 and shaft 2 are designed as disposable components. In this exemplary embodiment, the tip 10, the guide element 9 and/or the manipulator 13 consequently are firm, inseparable components of the disposable instrument. Into the disposable instrument there can also be integrated an insufflation channel 22 for the insufflation and a working channel 20 for the irrigation and/or aspiration.

Figure 8:
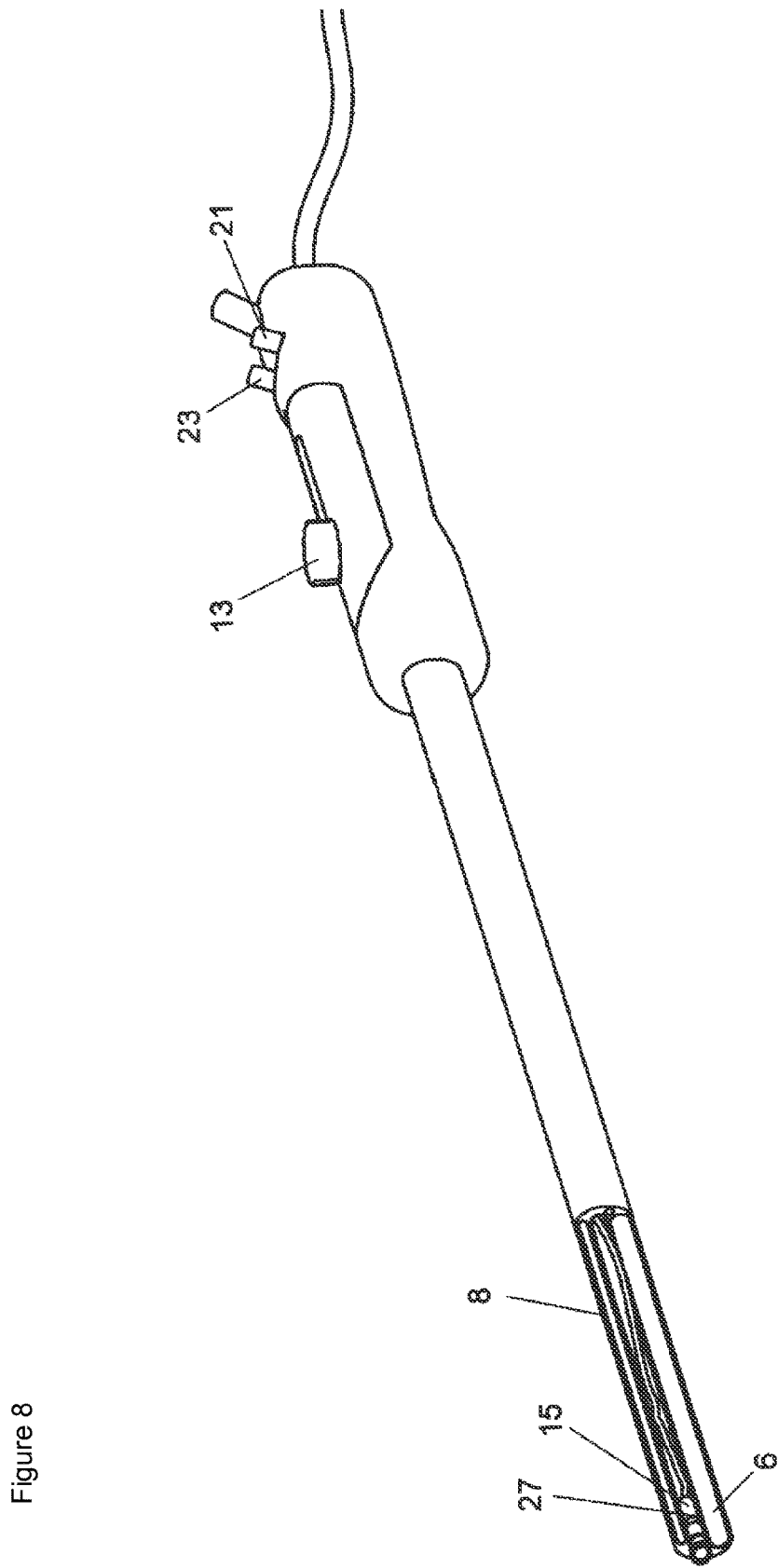
FIG. 8 shows an embodiment with a video interface.
Figure 9:
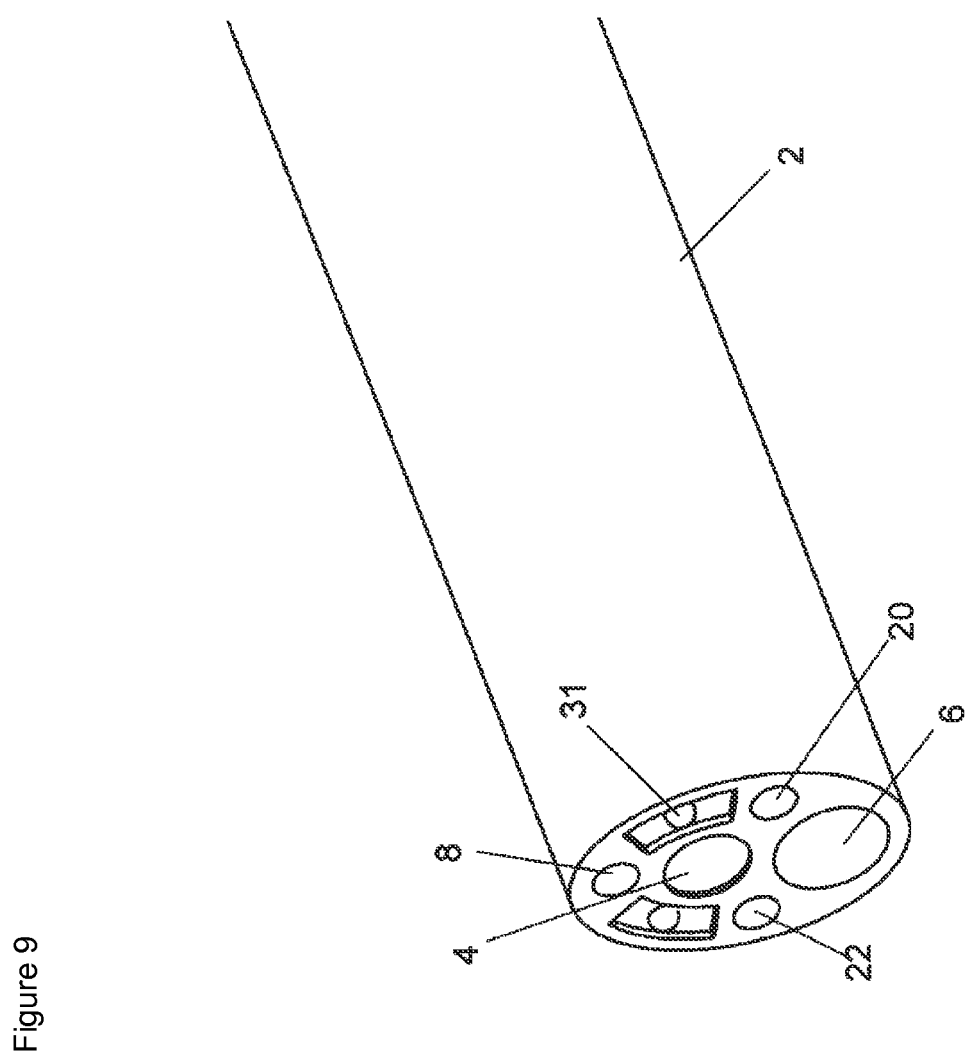
FIG. 9 shows an embodiment with a solid polymer rod as optical waveguide.

In a further exemplary embodiment (FIG. 8), the endoscope 5 can be replaced by a video camera 27 integrated at the instrument tip 15 or can be used together with the same. This video camera can include a video sensor, e.g. CCD or CMOS sensor, along with associated electronics and suitable optics. In the exemplary embodiment described here, the glass fibers 28 usually integrated in the endoscope 5, which serve the transmission of light for illuminating the operating field, are guided in a separate illumination channel 29 from the handle 3 via the shaft 2 to the instrument tip 15.

Figure 10:
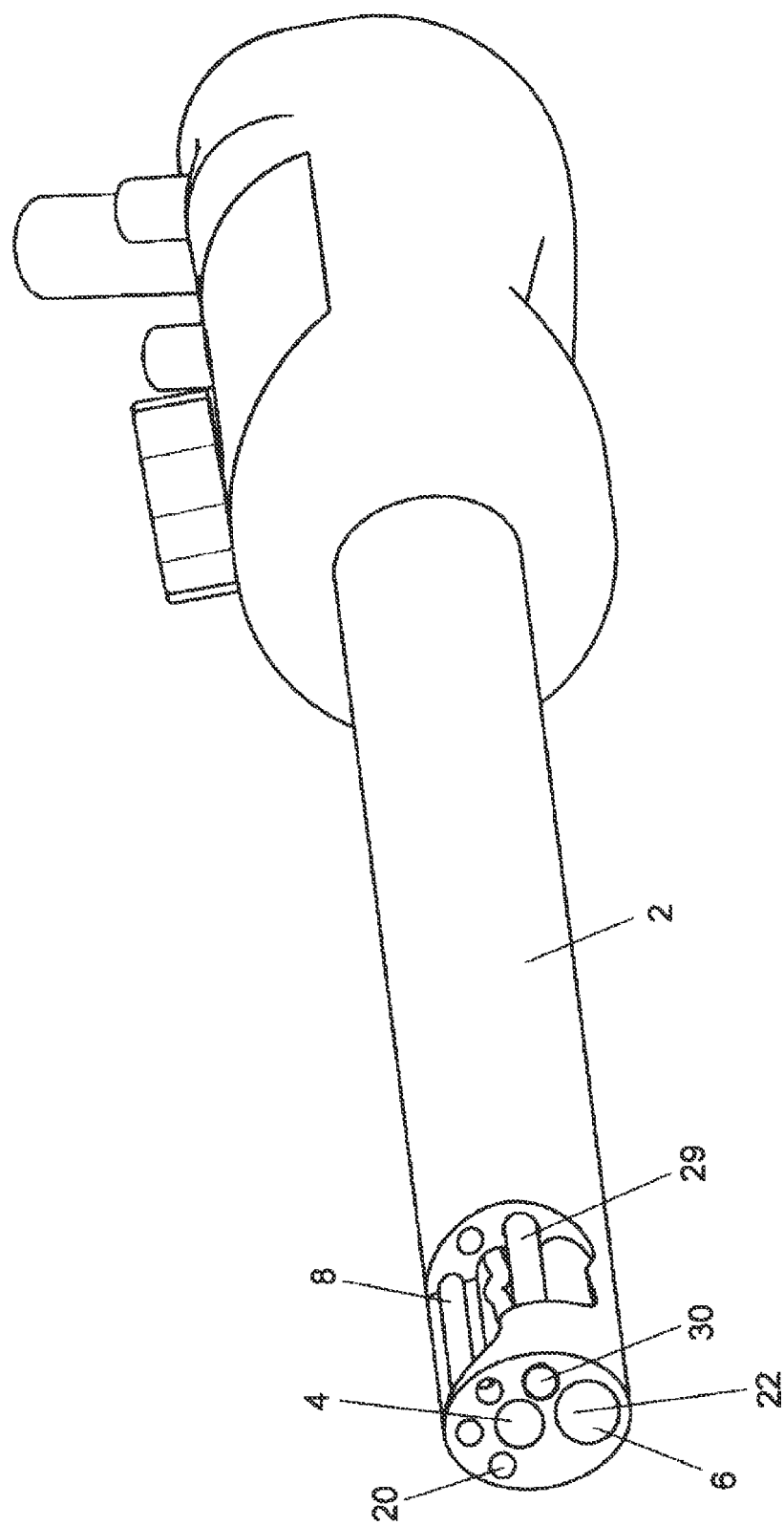
FIG. 10 shows an embodiment with LED at the tip.
Figure 11:
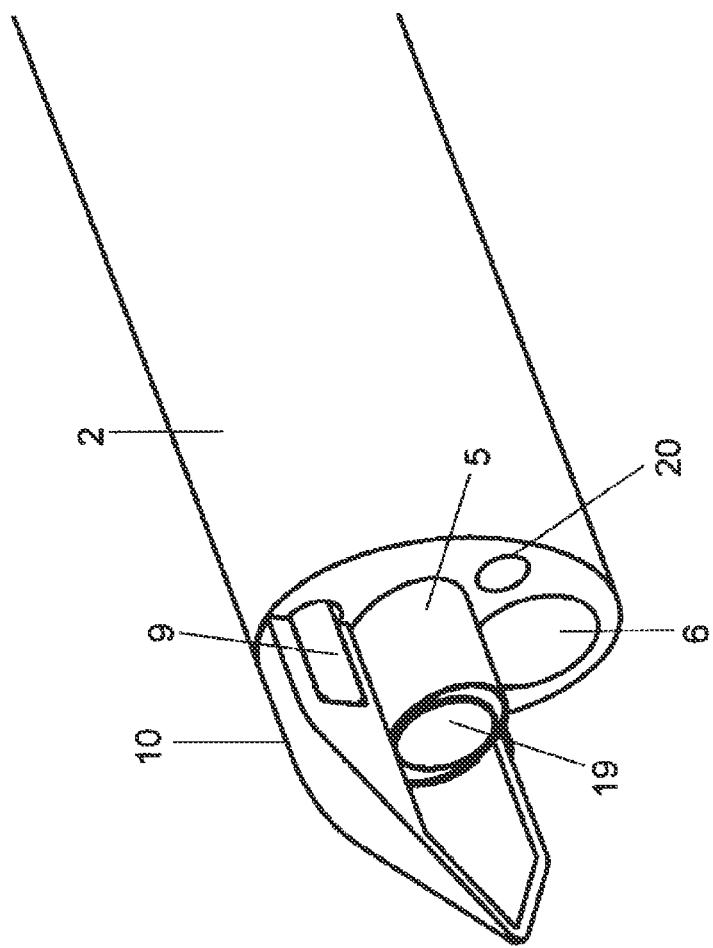
FIG. 11 shows a detail of a further embodiment.

In a further embodiment (FIG. 10), the glass fibers 28 in the disposable instrument are replaced by a solid polymer rod 30. The same can be designed in an arbitrary, space-saving shape which is suitable for conducting light. Alternatively or also in addition, a flexible optical waveguide of silicone or another suitable material can be used.

In a further exemplary embodiment, the glass fibers 28 in the disposable instrument are replaced by LEDs 31 positioned at the instrument tip 15. In principle, combination possibilities are also conceivable.

The same can be designed in an arbitrary, space-saving shape which is suitable for illuminating the field of view of the video camera 27.

Figure 13A:
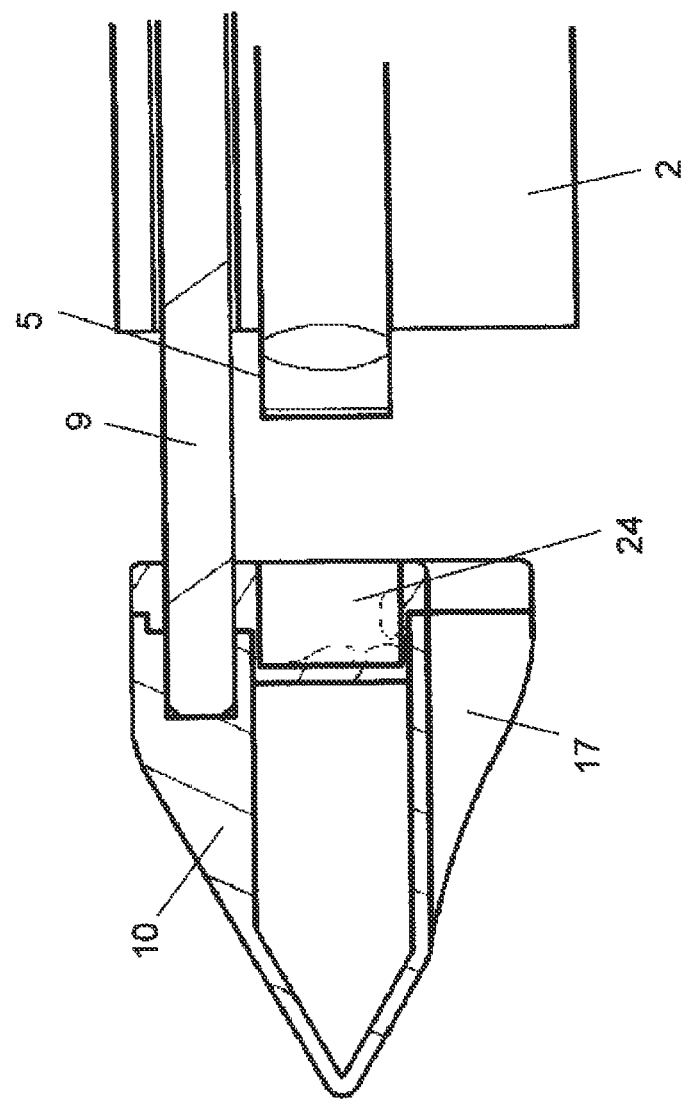
FIGS. 13a, b each show sectional views through the tip and the shaft of one embodiment.

FIGS. 13a, b show sectional views through a transparent tip 10 and a shaft 2, wherein here an endoscope 5 is shown as functional unit. In FIG. 13a, the transparent tip 10 is shown in the distal position. In a cutout 24 a few water droplets are shown, which are left on the inside of the tip 10 e.g. after the irrigation. The cutout 24 can be part of a baffle plate which is arranged at the proximal end of the tip 10. A further embodiment of this proximal baffle plate is shown in FIG. 14.

Figure 13B:
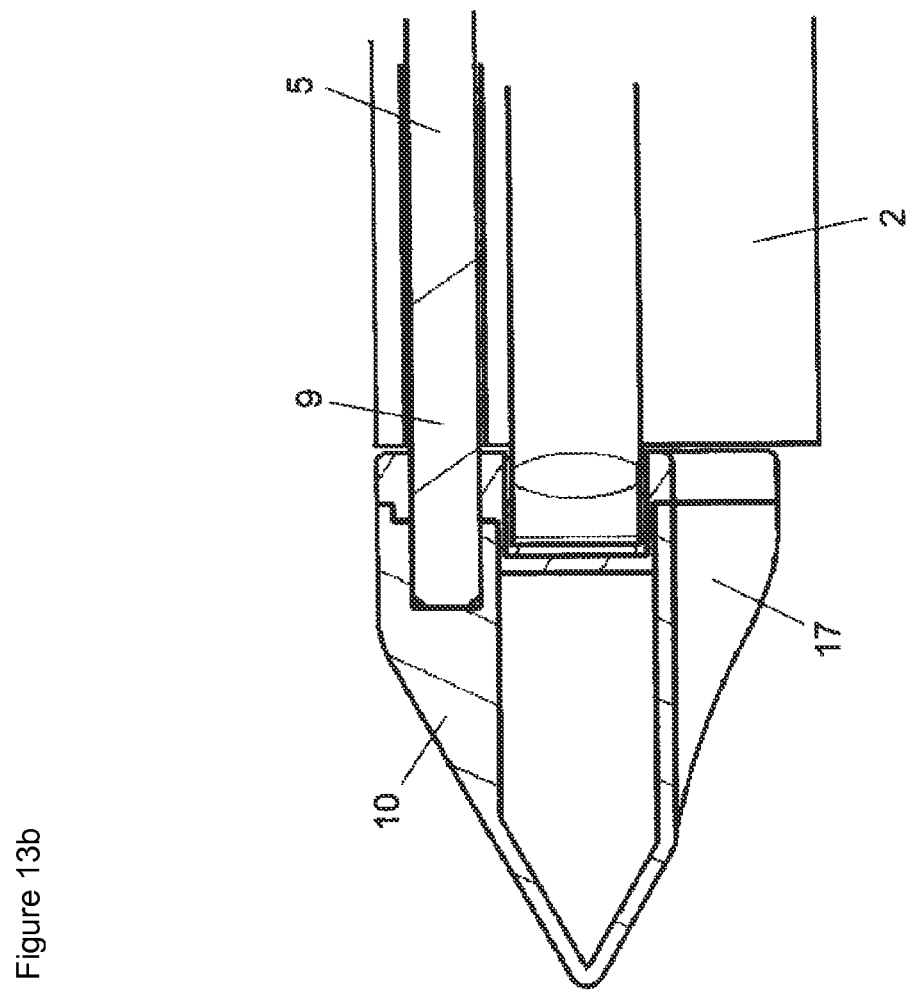

When the tip 10 now is brought into the proximal position (FIG. 13b), the tip of the endoscope 5 protrudes into the cutout 24. The protruding end of the endoscope 5 compresses the water droplets in the cutout 24, so that a substantially uniform film is obtained in the gap between the cutout 24 and the endoscope 5. This does not impair the optical properties. Furthermore, it can be seen in FIGS. 13a, b that the interior of the tip is formed substantially hollow, above all in the region which is located axially in the field of view of the endoscope 5.

Figure 14:
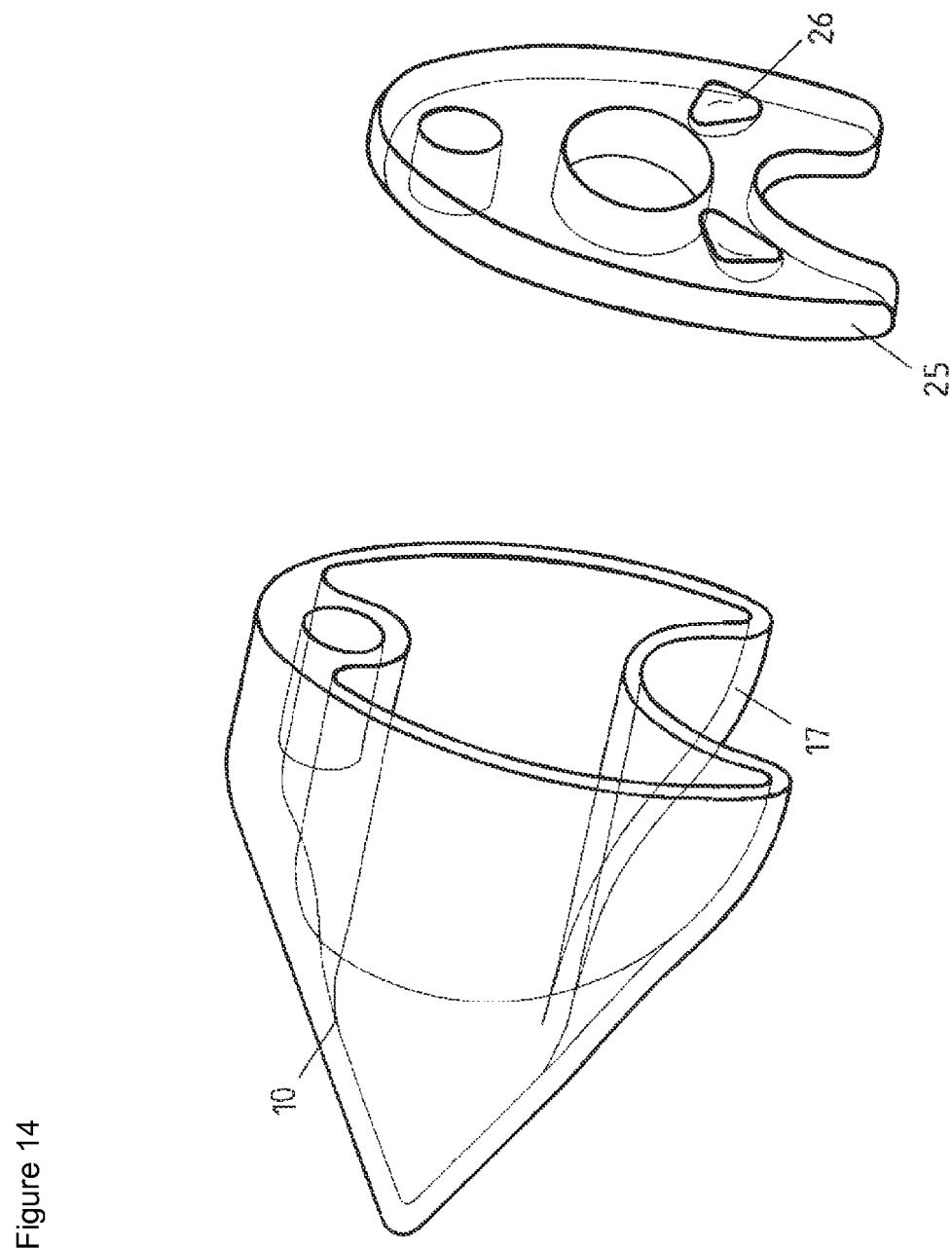
FIG. 14 shows an exploded drawing of an embodiment of a tip with a baffle plate.

In FIG. 14, a tip 10 is shown in the form of an exploded drawing, which is formed as free form. The diameter tapers from proximal to distal. The recess 17 points downwards. The interior of the tip 10 here is formed substantially hollow, wherein the wall thicknesses of the transparent material are substantially the same.

At the proximal end of the transparent tip 10 a baffle plate 25 is arranged, at which e.g. rinsing liquid can be diverted according to the procedure in FIG. 12, in order to selectively clean an endoscope 5. To support this cleaning, the baffle plate 25 includes at least one diverting means 26 with which the irrigation jet can selectively be directed to the endoscope 5. The diverting means 26 here is formed as depression. In principle, other forms which e.g. protrude beyond the base surface of the baffle plate 25 can also be used. Alternatively or in addition, other functional units such as e.g. the cutting device also can be cleaned by the irrigation jet.

LIST OF REFERENCE NUMERALS 1 instrument
2 shaft
3 handle
4 endoscope channel
5 endoscope
6 working channel
7 cutting device
8 guide channel
9 guiding device
10 transparent tip
11 opening of the endoscope channel
12 opening of the working channel
13 manipulator of the guiding device
14 vessel
15 instrument tip
16 instrument axis
17 vessel receiving means
18a retracted position of the tip
18b extended position of the tip
19 endoscope tip
20 irrigation channel
21 port of irrigation channel
22 insufflation channel 23 port of gas channel
24 cutout
25 baffle plate
26 diverting means
27 video camera
28 glass fibers
29 illumination channel
30 solid polymer rod
31 LED
40 secondary vessel

The invention claimed is:

1. An invasive instrument for treating a vessel, comprising:
   an elongated shaft having a proximal end and a distal end to be introduced into a body of a subject, the distal end having a working opening of a working channel that is located in the elongated shaft;
   a dissection tip coupled to a guide element that is operably coupled to the shaft so that the dissection tip has a retracted tip position proximal to the distal end of the shaft and a shifted tip position spaced apart from the distal end of the shaft that is shifted relative to the retracted position, wherein the dissection tip is transparent and is formed for the dissection of tissue, wherein the dissection tip includes an outer surface having at least one vessel receptacle formed into the outer surface;
   at least one functional unit operably coupled with the shaft so as to have a retracted functional position within a working channel of the shaft when the dissection tip is in the retracted tip position and have a dissection functional position when the at least one functional unit is extended from the distal end of the shaft when the dissection tip is in the shifted tip position such that the at least one vessel receptacle is spaced apart from the at least one functional unit; and
   an endoscope tip operably coupled with the shaft so as to protrude from the distal end of the shaft into the dissection tip when in the retracted tip position,
   wherein when in the retracted tip position the at least one vessel receptacle of the dissection tip is aligned with the working channel so that the at least one functional unit is movable relative to the dissection tip when the at least one functional unit is moved between an axially retracted position and an axially extended position distal to the tip or beyond the tip with the tip being in the retracted position.

2. The invasive instrument according to claim 1, wherein the dissection tip at least partly includes a conical region, a prismatic region, a region in the form of a dolphin nose, a region with a frustoconical shape or a region with the shape of a triangle.

3. The invasive instrument according to claim 1, wherein the dissection tip is pivotable about a longitudinal axis of the shaft by up to 180°, so that during a procedure a vessel arranged in the at least one vessel receptacle is spaced selectively from a cutting device of the functional unit.

4. The invasive instrument according to claim 1, further comprising:
   a handle at the proximal end of the shaft; and
   a manipulator arranged at the handle for axially shifting or rotating the dissection tip relative to the distal end of the shaft between the retracted tip position and the shifted tip position.

5. The invasive instrument according to claim 4, further comprising at least one endoscope channel, at least one working channel for receiving a cutting device, at least one guide channel for receiving the guide element, at least one irrigation channel or at least one insufflation channel arranged in the shaft or the handle, wherein the handle or the shaft are designed as a reusable instrument.

6. The invasive instrument according to claim 4, wherein the dissection tip, the guide element or the manipulator are designed as disposable components.

7. The invasive instrument according to claim 1, wherein the guide element is substantially rod-shaped and is attached at a point of the dissection tip which is located opposite of the vessel receptacle.

8. The invasive instrument according to claim 1, wherein the shaft includes at least one guide channel having the guide element and the at least one working channel having the at least one functional unit, arranged on opposite sides of the shaft.

9. The invasive instrument according to claim 1, wherein when in the retracted tip position the endoscope is aligned with the working channel so that the endoscope is movable relative to the dissection tip when the endoscope is moved between an axially retracted position and an axially extended position.

10. The invasive instrument according to claim 1, further comprising at least one channel having an opening at the distal end that is integrated into the shaft for conducting a rinsing liquid or for sucking off undesired liquids, wherein the shaft has an at least partly circular or elliptical cross-section.

11. The invasive instrument according to claim 1, further comprising an insufflation channel having an opening at the distal end that is integrated in the shaft such that a gas for insufflation can be passed from the distal end of the shaft.

12. The invasive instrument according to claim 11, wherein the insufflation channel is arranged relative to the endoscope tip such that the endoscope tip can be cleaned with the gas, in that the gas stream is diverted on the back of the dissection tip and directed to the endoscope tip.

13. The invasive instrument according to claim 1, further comprising a video camera located at the distal end of the shaft, wherein the video camera includes a video sensor, along with associated electronics and suitable optics, and glass fibers, a flexible optical waveguide or a solid polymer rod are located in a separate illumination channel of the shaft from the handle to the distal end of the shaft; or
   at least one LED is located at the distal end of the shaft for illumination.

14. The invasive instrument according to claim 1, further comprising an irrigation jet at the distal end of the shaft, wherein the dissection tip includes at least one diverter for the irrigation jet.

15. A surgical method performed with the invasive instrument according to claim 1, wherein:
   a) forming a cut into the skin of a body;
   b) introducing the dissection tip of the invasive instrument into the cut along a vessel, in order to separate surrounding tissue from the vessel;
   c) extending the at least one functional unit through the at least one vessel receptacle means when the dissection tip is in the retracted tip position; and
   d) treating tissue around the cut, a secondary vessel, or a vessel with the functional unit when the dissection tip is in the retracted tip position.

16. The surgical method according to claim 15, further comprising cleaning the at least one functional unit by a gas or a rinsing liquid after the dissection tip is introduced through the cut.

* * * * *